(12) United States Patent
Brau

(10) Patent No.: US 8,157,819 B2
(45) Date of Patent: Apr. 17, 2012

(54) ENCASEMENT PREVENTION BARRIER FOR USE IN ANTERIOR LUMBAR SURGERY

(76) Inventor: Salvador A. Brau, Los Angeles, CA (US)

( * ) Notice: Subject to any disclaimer, the term of this patent is extended or adjusted under 35 U.S.C. 154(b) by 1097 days.

(21) Appl. No.: 11/880,294

(22) Filed: Jul. 19, 2007

(65) Prior Publication Data

US 2008/0300595 A1    Dec. 4, 2008

Related U.S. Application Data

(60) Provisional application No. 60/932,921, filed on Jun. 4, 2007.

(51) Int. Cl.
*A61B 17/08* (2006.01)
*A61B 17/56* (2006.01)
*A61F 5/04* (2006.01)

(52) U.S. Cl. .......................... 606/151; 606/53

(58) Field of Classification Search ...... 606/53, 606/151
See application file for complete search history.

(56) References Cited

U.S. PATENT DOCUMENTS

| 5,868,745 | A | * | 2/1999 | Alleyne ............... 606/86 R |
| 6,039,763 | A | | 3/2000 | Shelokov |
| 6,416,465 | B2 | | 7/2002 | Brau |
| 6,475,219 | B1 | * | 11/2002 | Shelokov ............... 606/281 |
| 2005/0126576 | A1 | | 6/2005 | Ferree |
| 2007/0055111 | A1 | * | 3/2007 | Morgan et al. ............ 600/235 |
| 2007/0297987 | A1 | | 12/2007 | Stad et al. |
| 2008/0107711 | A1 | | 5/2008 | Shelokov |
| 2008/0119851 | A1 | | 5/2008 | Shelokov |

FOREIGN PATENT DOCUMENTS

WO    WO 2007/030242 A1    3/2007

OTHER PUBLICATIONS

Hydrosorb® Shield Bioresorbable Implant (Advertisement—1 p.); Part # 6651357; ©2005; for more information go to www.myspinetools.com.
Gore Preclude® Vessel Guard—brochure; 2 pages.
"Gore Preclude Vessel Guard Reduces Vascular . . . " http://www.goremedical.com/vesselguard; 2 pages.
Gore Preclude® Vessel Guard Instructions for Use for; use instructions at http://www.goremedical.com/en/ifu/AK0993.pdf; 4 pages.

* cited by examiner

*Primary Examiner* — Thomas C. Barrett
*Assistant Examiner* — Christine Nelson
(74) *Attorney, Agent, or Firm* — Christie, Parker & Hale, LLP

(57) ABSTRACT

A flexible piece of barrier material for use in preventing or minimizing adhesions and fibrous attachments following anterior lumbar surgery. In one embodiment, the barrier structure comprises a multiple level device shaped as a generally wider tongue to function as a barrier at or above the L4-5 level, and a generally narrower lower section to function as a barrier at or below the L5-S1 level. The structure also can include a recessed waist section along an edge opposite the tongue to allow for easier placement in the L4-5 area. In another embodiment, a single level barrier for use at or above L4-5 is shaped as a tongue with a tapered outer extension to allow the barrier to extend laterally onto the psoas muscle to provide for identification of the barrier upon reoperation.

6 Claims, 2 Drawing Sheets

ENCASEMENT PREVENTION BARRIER FOR USE IN ANTERIOR LUMBAR SURGERY

CROSS-REFERENCE TO RELATED APPLICATION

This application claims priority to Provisional Application No. 60/932,921, filed Jun. 4, 2007, incorporated herein by this reference.

FIELD OF THE INVENTION

This invention relates to an improved encasement prevention barrier for use in preventing or minimizing adhesions and fibrous attachments following anterior lumbar surgery.

BACKGROUND

Spine surgery, such as vertebral fusions, is common and is becoming more reliable as better methods are developed for stabilizing the back and improving bone grafts, for example, to repair disc injuries, vertebral fractures, and the effects of osteoarthritis. Many spine surgeries require an anterior approach, such as those for degenerative disc disease (both denovo and to correct failed prior back surgery), and for infected discs, tumor removal and scoliosis (e.g., for excision, drainage, or decompression).

Anterior fusions are often preferable to posterior fusions because the bone surface area available for the fusion is considerably larger, and any discs to be removed are more accessible. This makes the likelihood of successful fusion greater; and the time required for the operation less, translating to less time that the patient is under general anesthesia.

A surgical implement and surgical access method for anterior lumbar surgery are described in my U.S. Pat. Nos. 6,296,609 and 6,416,465, the disclosures of which are incorporated herein by this reference.

Adhesions and/or fibrous attachments can develop following anterior lumbar surgery, be it fusion, disc replacement, nucleus replacement, or any other anterior lumbar procedure that requires dissection of the anterior surface of the spine to obtain access to the disc spaces. This invention has to do with a barrier placed into position, following the spinal procedure, between the anterior surface of the spine and one or more of the following structures: the blood vessels such as the aorta, inferior vena cava, common iliac arteries, common iliac veins, or other structures such as the ureter and nerve fibers. The barrier can prevent or minimize encasement of all these structures by scar tissue formation, fibrosis and adhesions, which present a significant risk of re-exposure should the need arise to return to this same area of the spine or adjacent areas in the future.

GLOSSARY OF TERMS

For the purposes of this application, the following glossary describes the terminology used herein, so as to better explain how to make and use the invention.

Adhesions—Formation of scar tissue after an operation causes adjacent tissues to adhere to each other, thus the term adhesions.

Fibrosis—Most scar tissue is produced by fibroblasts, which set down fibers of whitish tissue as part of the healing process.

Lumbar spine—The vertebral column from the L1 vertebra to the S1 vertebra.

Disc spaces—The space between vertebral bodies occupied by the disc. E.g. The disc between the L4 vertebra and the L5 vertebra is the L4-5 disc space. The disc between the L5 vertebra and the S1 vertebra is the L5-S1 disc space.

Left iliac vessels—These are the major vessels that branch off the Abdominal Aorta and the Inferior Vena Cava. The left iliac artery feeds to the left lower extremity and left side of the pelvis. The left iliac vein drains the left leg and left side of the pelvis. These vessels course directly above the L5 vertebra as well as portions of the L4-5 and L5-S1 disc spaces and are in close contact with these structures. They must be widely mobilized in order for a spine surgeon to perform surgery on these disc spaces. Because of fibrosis and adhesions, they become extremely difficult to re-mobilize if a re-operation of these disc spaces becomes necessary.

Ureter—Tubular structure that carries urine from the kidney to the bladder. It lies over the psoas muscle, has to be mobilized for anterior lumbar surgery and gets bound by adhesions following that surgery.

Psoas muscle—Courses along the lateral surface of the spine and inserts into L1. It is a landmark used by the access surgeon to help identify the antero-lateral surface of the vertebral column and the disc spaces. Adhesions form on it following anterior lumbar spine surgery making it extremely difficult to re-enter the retroperitoneal space on a re-operation.

Left sympathetic chain—The main trunk of sympathetic fibers that run along the antero-lateral surface of the spine and send branches from there to the different organs as part of the "autonomic nervous system."

SUMMARY OF THE INVENTION

Briefly, the invention comprises flexible profiled piece of barrier material for use in preventing or minimizing adhesions and fibrous attachments following anterior lumbar surgery. In one embodiment, the barrier structure has a size and shape (i.e., two dimensional profile) that facilitates use in single level spinal procedures or multiple level procedures at and above L4-5. In another embodiment, the barrier structure has a size and shape (or profile) that facilitates use at the L4-5, L5-S1 levels when these two levels are approached simultaneously.

In the embodiment in which the barrier structure comprises a multiple level device, the barrier is shaped to form a generally wider-extension or tongue that functions as a barrier at or above the L4-5 level, and a generally narrower lower section that functions as a barrier at or below the L5-S1 level. The elongated tongue section extends laterally onto the psoas muscle during use, to provide for identification of the barrier upon reoperation. The barrier structure also can include a recessed waist section along an edge opposite the tongue to allow for easier placement in the L4-5 area. In the single level embodiment, the barrier is shaped for use at or above the L4-5 level, and comprises a tongue-shaped structure with a tapered outer extension to allow the barrier to extend laterally onto the psoas muscle.

These sizes and shapes or configurations and other features of the barrier are designed to make optimal use of the barrier in terms of identification of the barrier initially, orientation of the surgeon after identification, and ease of dissection and use as a tissue separator, once identified.

The shape applies to a barrier made of any material known today or to be developed in the future, which may be deemed effective in preventing or diminishing the risks of injury to the structures mentioned above and which may be useful in minimizing the risk of re-exposure.

DETAILED DESCRIPTION

Figure 1:
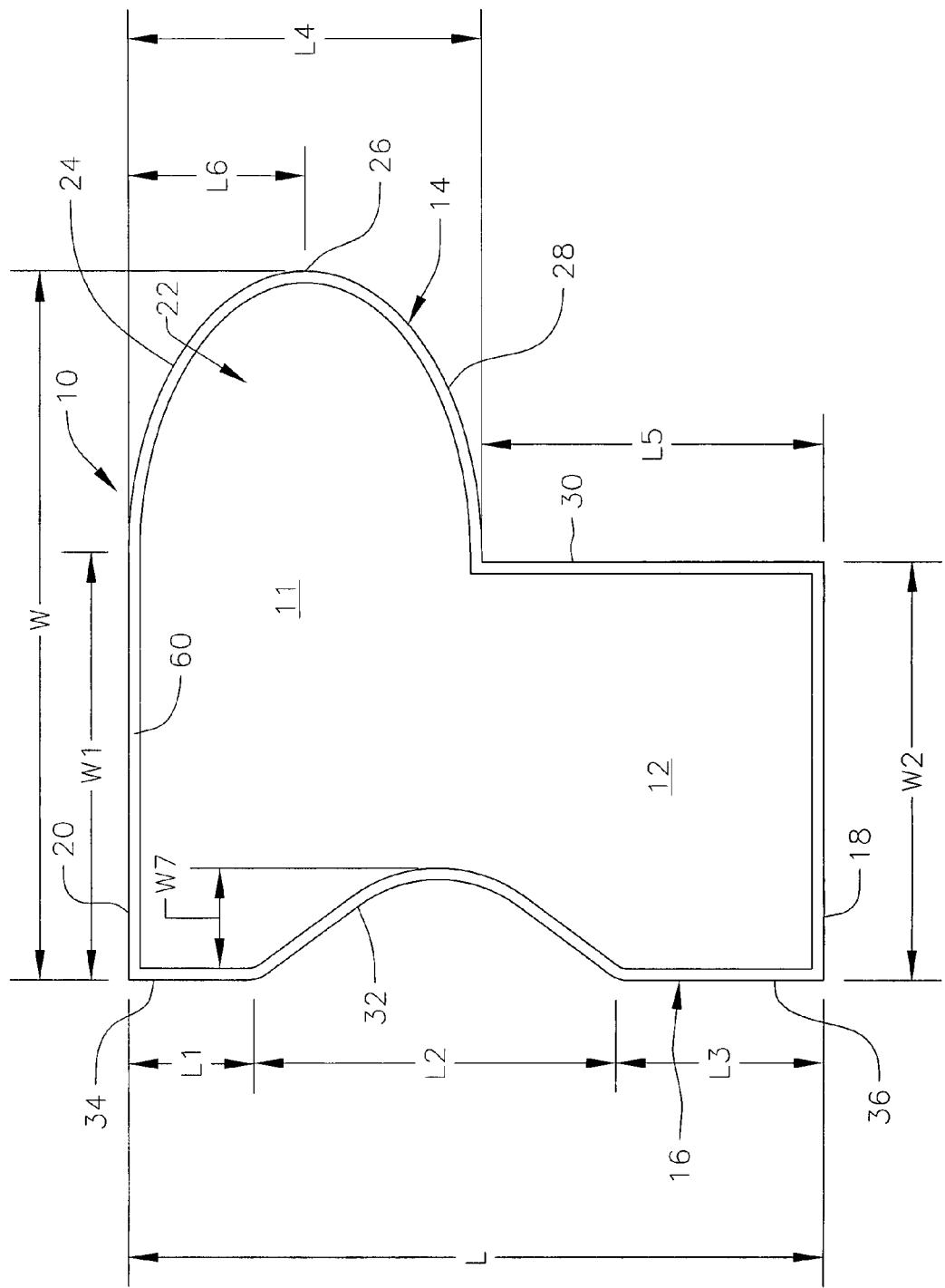
FIG. 1 is an elevational view showing a first embodiment of the invention useful as a multiple level barrier device.

Referring to FIG. 1, a multiple level barrier 10 comprises a unitary construction having an upper section 11 and a lower section 12. A first marginal edge 14 extends along a right side of the structure and a second marginal edge 16 extends along a left side of the structure. The barrier has an overall height L extending from a flat bottom edge 18 of the lower section 12 to a flat top edge 20 of the upper section 11. The barrier has a first width W extending across the upper section 11 between the first marginal edge 14 and the second marginal edge 16. The barrier has a second width W2 extending across the lower section 12 between the first and second marginal edges. The width W of the upper section 11 is greater than the width W2 of the lower section.

The wider upper section 11 is shaped generally as a laterally extending tongue 22 having a first marginal edge portion projecting laterally beyond the first marginal edge portion of the lower section 12. The first marginal edge portion of the tongue is generally rounded, formed by a tapered upper portion 24 curving downwardly and outwardly to an intermediate level at 26, where it forms the maximum width of the barrier's upper section 11. The rounded tongue is further formed by a first marginal edge portion 28 transitioning to taper downwardly and inwardly to a first marginal edge portion 30 of the lower section 12. The top edge 20 is generally straight and is defined by a width W1 which then transitions to the rounded, laterally projecting portion of the tongue. The height of the tongue (or upper section 11) is defined by the dimension L4, and the height of the lower section 12 is defined by the dimension L5. The height of the rounded upper portion of the tongue is defined by the dimension L6.

The left side of the barrier along the second marginal edge 16 is profiled to form a recessed waist section 32 at an intermediate level between the top edge 20 and the bottom edge 18 of the barrier. The waist section 32 is formed in an intermediate portion of the second marginal edge 16, with the second marginal edge being formed by a straight upper section 34 defined by the dimension L1, transitioning to the waist having its height defined by the dimension L2, followed by a lower straight edge portion 36 defined by the dimension L3. The flat lower edge portion 36 is generally aligned with the flat upper edge portion 34 of the left marginal edge.

Figure 2:
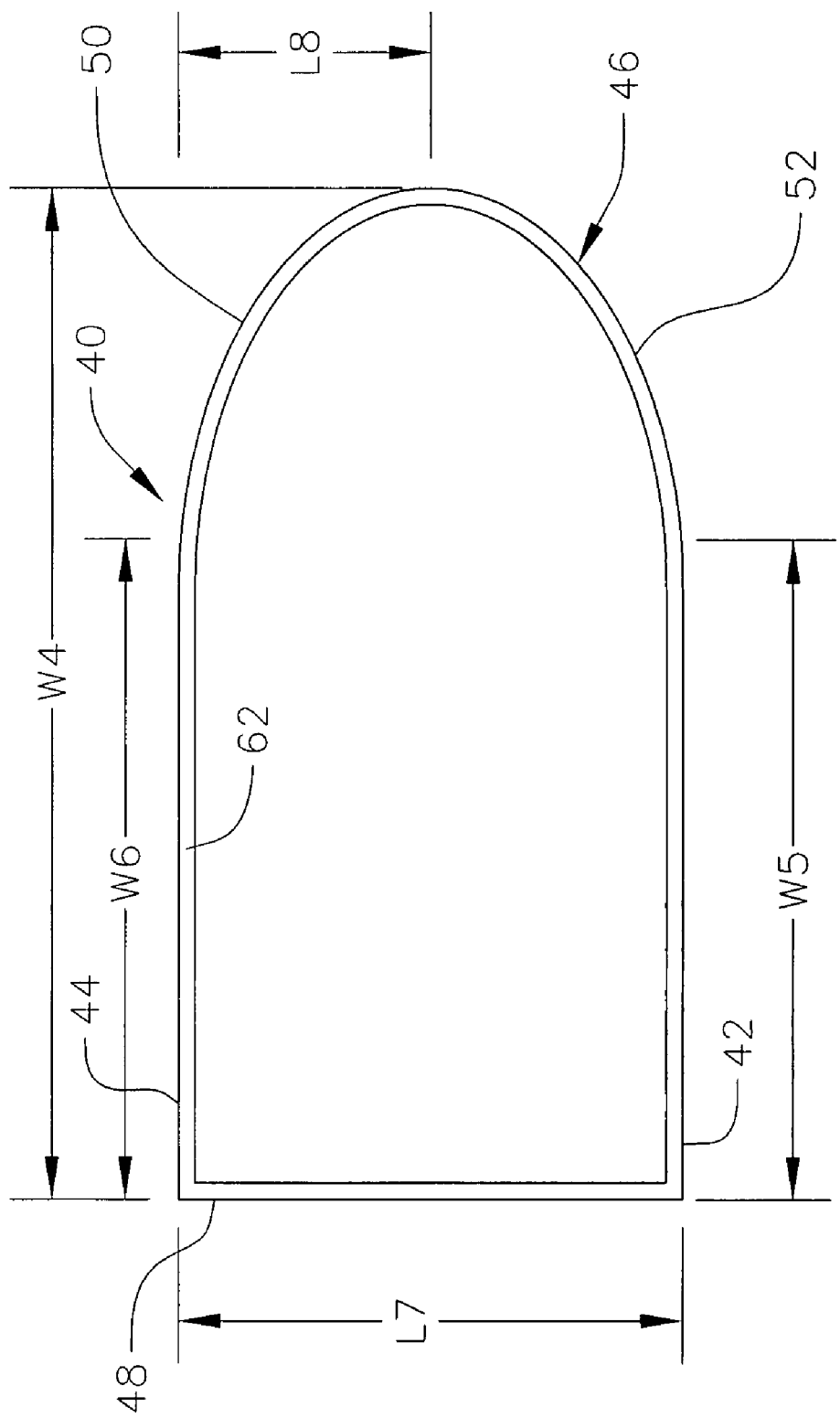
FIG. 2 is an elevational view showing a second embodiment of the invention useful as a single level barrier device.

FIG. 2 illustrates a single level barrier structure 40 for use as an encasement prevention barrier at or above the L4-5 level in anterior lumbar surgery. The barrier 40 comprises a unitary structure having a height L7 extending from a bottom marginal edge 42 to a top marginal top edge 44 of the barrier. A first marginal edge 46 extends the height of the barrier structure along one side of the structure. A second marginal edge 48 extends the height of the barrier structure along an opposite side of the barrier. The maximum width W4 of the barrier structure is formed along an intermediate level between the marginal edges 46 and 48. The width of the barrier is greater than the height of the barrier. The barrier is shaped generally as a tongue similar to the FIG. 1 structure, in which the first marginal edge 46 is generally rounded, having a tapered upper portion 50 above an intermediate region of maximum width, and a tapered lower section 52 below the intermediate region of maximum width. The upper edge 44 of the tongue extends along a generally straight path defined by the dimension W6, transitioning into the rounded tongue portion and then to a straight portion of the lower edge defined by the dimension W5. The height of the rounded upper portion of the tongue is defined by the dimension L8.

At the present time, a permanent, non-resorbable barrier, and other non-resorbable barriers are being supplied in conventional, rectangular shapes. These shapes fail to take into account that scar tissue deposition and adhesions can form in areas outside the scope of these shapes. The present invention addresses these problems and provides improvements in reducing the difficulty of reoperation.

The barrier profile with the tongue-shaped barrier extended laterally to the left can prevent adhesions from forming over the left psoas muscle, under the ureter and over the left sympathetic chain. The ureter is a structure at great risk of injury during a reoperation, especially at disc spaces L4-5 and higher. The psoas is an important landmark used by surgeons to help identify the antero-lateral surface of the spine in reoperative cases. The sympathetic chain is almost invariably injured during reoperative cases because it becomes indistinguishable from other tissues and also becomes very adherent to the anterior surface of the spine from adhesions.

The barrier shaped according to this invention can help prevent adhesions to the ureter and the sympathetic chain, thus protecting them from injury. It can also make easier the identification of the psoas further away from the edge of the spine. This provides an added degree of safety to any reoperative procedure that requires an anterior approach to the lumbar spine, by allowing the surgeon to find the psoas laterally and "follow" it to the edge of the spine and to the vessels.

Standard rectangular shapes do not offer this added benefit. If a rectangle is made bigger to try to obtain these benefits, the size can be too large and unwieldy, it will not fit properly under the vessels, it may crumple and defeat the purpose of a smooth barrier, and it can be more difficult and time consuming for the surgeon to deploy properly.

The barrier profile having the waist section 32 is useful for levels L4-5 and L5-S1. The lateral "room" under the vessels at these levels takes advantage of a tapering of the shape of the rectangle for the barrier to fit properly. The waist section allows for easier placement as it will not require additional mobilization of the vessels to the right in order to accommodate that wider barrier. It also allows for the barrier to remain smoothly applied without crumpling under the vessels.

During use, the barrier goes on the anterior surface of the spine and lies immediately beneath the great vessels, such as the iliac vein and artery or the aorta and vena cava, depending on the level being operated on. The recessed area of the barrier is useful when bringing the barrier under the vessels. Since the vessels may not be mobilized fully to the right, there is less space and the barrier tends to bunch up there. The waist section 32 keeps it from doing that and fitting more smoothly.

The anatomical coverage for L4 to S1 is the lower edge of the L4 vertebral body superiorly to the upper edge of the sacrum inferiorly, and from the right edge to the left edge of the vertebral body, in a rectangular barrier. With the barrier shaped according to this invention, the tongue extends to cover part of the belly of the psoas muscle as well, and the waist would allow for a better fit under the iliac vessels.

There are, at the present time, three types of material that can be used as barriers to try to prevent encasement of the vascular structures and other tissues by scar tissue formation and fibrosis after anterior lumbar surgery. One of these materials, Preclude Vessel Guard (Gore, Inc.), has been approved by the Food and Drug Administration (FDA) for this particular application. Of the other two materials, Hydrosorb (Medtronic Sofamor Danek) has not been approved by the FDA for this application and is being used in an "off-label" fashion. The third material is small intestinal submucosa (SIS), which is not FDA approved either.

The Gore barrier is made of PTFE (expanded Teflon) and is microporous on both surfaces, thus preventing tissue ingrowth. It remains in the area where it has been applied and may act as a separator, which then can be used to mobilize the vessels and other structures from the anterior surface of the spine in case of reoperation. It is currently provided in rectangular shapes of 5×6 cm and 10×6 cm×0.2 mm thin.

Hydrosorb is made of polylactic acid and is a resorbable in nature. It is present when scar tissue is being deposited in the operative area and is then resorbed by the body, hopefully leaving the area free of adhesions. It is supplied as a film in one rectangular size of 5 cm×7 cm×0.02 mm thin.

The small intestinal submucosal barrier is also resorbable and very similar to Hydrosorb in its mode of action and is also supplied as a film of varying rectangular sizes.

Any barrier materials developed in the future would be expected to have similar modes of action to the present ones. They would either be permanent materials that provide a physical barrier to be found in future reoperations or resorbable materials that would prevent or reduce the formation of adhesions between the vessels, ureter and nerve fibers to the anterior surface of the spine in the operated area.

In general, permanent barrier materials useful with this invention should have properties, such as microporosity, that would prevent scar tissue ingrowth and keep adhesions from forming between adjacent structures, which could be encased by scar tissue following an operation. Resorbable materials would prevent adhesions by not allowing the scar tissue to encase the structures involved while the body is producing scar tissue. Once this process is over, the barrier would disappear and leave the area in a condition hopefully similar to that of an "unoperated" state.

EXAMPLES

Generally speaking, the embodiments of the barrier structures 10 and 40 have the following size and shape or configuration, although the following descriptions, dimensions and sizes, etc., can vary without departing from the scope of the invention.

In the FIG. 1 barrier, the recessed waist extends for a height of about 40% to about 60% of the total height of the barrier. The tongue section also has its height extending from about 40% to about 60% of the overall height of the barrier. In one embodiment, the width of the upper tongue section 11 of the barrier compared to the width of the lower section 12 is defined by a ratio from about 1.8:1 to about 1.4:1. In another embodiment the relative width measurements are defined by a ratio from about 2:1 to about 3:2. The ratio of the width W to the length L4 of the upper section 11 is from about 2.5:1 to about 1.8:1.

In the FIG. 2 barrier the ratio of the width W4 to the length L7 is from about 2.5:1 to about 1.8:1.

The following examples describe the present best mode contemplated for carrying out the invention.

Example 1

A two-level, L4-5, L5-S1 barrier as shown in FIG. 1 is described as follows:

(1) The barrier structure is colored in light green or blue (or any other color other than red or yellow that will diminish the barrier from normal tissues) with a 2 mm border 60 of dark green or blue to identify the edges from the body of the barrier.

(2) 0.1 to 5 mm thick depending on the material to be used for the barrier.

(3) 9.5 to 10.5 cm high (dimension L) at its highest point with two widths.
  (a) The upper section 11 has a width of 9-10 cm (dimension W) with a tapered tongue starting at 58-60 mm (dimension W1) from the left edge and ending with a height of 2 cm (dimension L6). This upper section is 4-5 cm high (dimension L4).
  (b) The lower section is 58-60 mm wide (dimension W2) and 4-5 cm high (dimension L5).
  (c) The upper width W1 and lower width W2 are approximately the same.

(4) On the left margin a curved waist starts at 2 cm (dimension L1) from the upper left hand corner and extends for 5 cm (dimension L2) ending at 3 cm from the lower left hand corner (dimension L3). This waist extends into the body of the barrier for 12 to 15 mm (dimension W7), gently curving in and back out at the points mentioned.

(5) The purpose of the tongue on the upper portion is to allow for the barrier to extend laterally on to the psoas muscle and there act as an early point of identification of the barrier upon re-operation.

(6) The purpose of the waist on the mid left edge of the barrier is to allow for easier placement under the iliac vessels, which are sometimes not fully separated from the anterior surface of the spine on the right side of L5 and the L4-5 disc.

Example 2

The single level and multiple level above L4-5 barrier as shown in FIG. 2 is described as follows:

(1) The barrier structure is colored in light green or blue (or any other color other than red or yellow that will distinguish the barrier from normal tissues) with a 2 mm border 62 of dark green or blue to identify the edges from the body of the barrier.

(2) 0.1 to 5 mm thick depending on the material to be used for the barrier.

(3) 4 to 5 cm high or long (dimension L7) with a tapering right edge starting at 58 to 60 mm from the left edge (dimension W6) and ending at 9 to 10 cm from the right edge (dimension W4), with the taper down to 2 cm in height (dimension L8) at the left edge.

(4) 9-10 cm wide (dimension W4) with the tapered edge 50 on the right.

(5) The purpose of the right side extension as a tongue is to allow placement over the psoas muscle to act as an early identifier of the barrier upon re-operation.

What is claimed is:

1. A multi-function barrier for use in anterior lumbar surgery, the barrier comprising a unitary structure having a height defined by a top edge spaced above a bottom edge, and a width defined by a first marginal edge spaced laterally from a second marginal edge, the unitary structure comprising a flexible piece of an adhesion-inhibiting material which, in a unitary planar form thereof, has a flat two-dimensional profile forming an upper section continuous with a lower section extending along the height of the structure between the top and bottom edges thereof, and a lateral extension of the upper section projecting across the width of the structure between the first and second marginal edges thereof, the upper section having a height extending for about one-half the height of the structure from the top edge thereof to an intermediate level of the structure, the lower section having a height extending for about one-half the height of the structure from the bottom edge thereof to the intermediate level of the structure, the upper section adapted for placement along the L4-5 disc space between the spine and the great vessels, the lower section adapted for placement along the L5-S1 disc space between the spine and the great vessels, the lateral extension of the upper section transitioning outwardly along the first marginal edge from adjacent the top edge of the structure to a maximum width spaced laterally outward from the lower section, the lateral extension then transitioning inward to a juncture with the lower section near the intermediate level of the structure, the lateral extension thereby having a combined height and width adapted to extend outwardly adjacent to the ureter, the left sympathetic chain and onto the psoas to inhibit adhesions thereon, the second marginal edge of the structure having an inwardly extending recess which, in the flat unitary planar two-dimensional profile of the structure, extends into a lower portion of the upper section and downward across the intermediate level of the structure to form a recessed waist section having a sufficient depth to reduce mobilization of the great vessels on at least the right side of the L4-5 disc space when positioning the barrier between the spine and the right-side great vessels during use, in which the recessed waist section extends for a height of approximately 40% to 60% of the total height of the barrier structure, in which the depth of the recess is from about 20% to about 30% the width of the lower section of the barrier structure, and in which the lateral extension has its maximum height corresponding to the height of the L4-5 disc space, from which top and bottom edges of the lateral extension taper gradually outward to its maximum width which is spaced laterally outward from the first marginal edge of the lower section by a distance of at least about one-half the width of the lower section.

2. The barrier according to claim 1, in which the ratio of the maximum width of the upper section and its lateral extension to the width of the lower section is selected from the group consisting of:
(a) 1.8:1 to 1.4:1; or
(b) 2:1 to 3:2.

3. The barrier according to claim 1, in which the lateral extension has its maximum height extending for about 40% to about 60% the maximum height of the barrier structure.

4. The barrier according to claim 3, in which the ratio of the width of the upper section and its lateral extension to the length of the upper section is from about 2.5:1 to about 1.8:1.

5. The barrier according to claim 1, in which the maximum width of the lateral extension is spaced laterally outward from the lower section by a distance of at least about 3 cm.

6. The barrier according to claim 1, in which the lateral extension has an outer region with an identifying color different from the color of a remaining portion of the lateral extension.

* * * * *